US00PP34693P2

(12) United States Plant Patent
Smit

(10) Patent No.: US PP34,693 P2
(45) Date of Patent: Oct. 25, 2022

(54) ***PEPEROMIA* PLANT 'EC-PEPE-2102'**

(50) Latin Name: *Peperomia caperata*
Varietal Denomination: EC-PEPE-2102

(71) Applicant: Eden Collection, BV, Sappemeer (NL)

(72) Inventor: Obed Smit, Sappemeer (NL)

(73) Assignee: Eden Collection B.V.

( * ) Notice: Subject to any disclaimer, the term of this patent is extended or adjusted under 35 U.S.C. 154(b) by 0 days.

(21) Appl. No.: 17/677,306

(22) Filed: Feb. 22, 2022

(51) Int. Cl.
*A01H 5/12* (2018.01)
*A01H 6/00* (2018.01)

(52) U.S. Cl.
USPC ..... Plt./373

(58) Field of Classification Search
USPC ..... Plt./373
See application file for complete search history.

*Primary Examiner* — Susan McCormick Ewoldt
(74) *Attorney, Agent, or Firm* — Cassandra Bright

(57) ABSTRACT

A new and distinct cultivar of *Peperomia* plant named 'EC-PEPE-2102' is disclosed, characterized by rosette-shaped, compact habits, which are ideal for small pots. Oval-shaped leaves with two contrasting colors: dark-green around leaf veins, and silver-grey in between veins. The new variety is a *Peperomia*, typically used as an ornamental plant.

3 Drawing Sheets

Latin name of the genus and species: *Peperomia caperata.*
Variety denomination: 'EC-PEPE-2102'.

BACKGROUND OF THE INVENTION

The new cultivar is a product of a planned breeding program to produce distinct and better performing *Peperomia* varieties. The new variety was selected as a seedling resulting from the crossing of *Peperomia caperata* '#014', and '#007', two unpatented varieties from the inventor's breeding line. The crossing was made by the inventor, Obed J. Smit, a citizen of the Netherlands in 2018. 'EC-PEPE-2102' was selected by the inventor in 2020 at a commercial greenhouse in Sappemeer, the Netherlands.

Asexual reproduction of the new cultivar 'EC-PEPE-2102' by terminal cuttings was first performed in Sappemeer, the Netherlands at a commercial greenhouse in March 2020, and has shown that the unique features of this cultivar are stable and reproduced true to type through successive generations.

SUMMARY OF THE INVENTION

The cultivar 'EC-PEPE-2102' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'EC-PEPE-2102'. These characteristics in combination distinguish 'EC-PEPE-2102' as a new and distinct *Peperomia* cultivar:

1. Leaves have two contrasting colors: dark-green around leaf veins, and silver-grey in between veins.
2. Oval-shaped leaves.
3. Rosette-shaped compact habit, ideal for small pots.

PARENT COMPARISON

Plants of the new cultivar 'EC-PEPE-2102' are similar to plants of the female parent, *Peperomia caperata* '#014' in most horticultural characteristics, however, plants of the new cultivar 'EC-PEPE-2102' differ from in the following characteristics:

1. Leaves of the new variety are oval-shaped, while leaves of the seed parent are less oval with a pointed tip.
2. Leaves of the new variety have two contrasting colors of dark-green around main leaf veins, and silver-grey in between main leaf veins. Leaves of the seed parent are a lighter tone of grey-green.
3. The new variety has many leaves, forming a dense rosette. The seed parent has fewer leaves, making a less dense rosette.

Plants of the new cultivar 'EC-PEPE-2102' are similar to plants of the male parent, *Peperomia caperata* '#007' in most horticultural characteristics, however, plants of the new cultivar 'EC-PEPE-2102' differ in the following characteristics:

1. Leaves of the new variety are oval-shaped, while leaves of the pollen parent are pointed.
2. Leaves of the new variety have two contrasting colors of dark-green around main leaf veins, and silver-grey in between main leaf veins. Leaves of the pollen parent are dark-green.
3. The new variety has a more compact habit than the pollen parent.

COMMERCIAL COMPARISON

Plants of the new cultivar 'EC-PEPE-2102' are similar to plants of the commercial variety *Peperomia* 'EC-PEPE-1904', U.S. Plant Pat. No. 32,564. However, plants of the new cultivar differ in the following characteristics:

1. Leaves of the new variety are smaller than leaves of this comparator.
2. The new variety has a smaller plant habit than that of this comparator.
3. Leaves of the new variety have a smoother surface than leaves of this comparator.

4. Leaves of the new variety have two contrasting colors of dark-green around main leaf veins, and silver-grey in between main leaf veins. Leaves of this comparator have two contrasting colors of dark-green around main and secondary leaf veins, and silver-grey in between all these veins, as little grey "islands."

Plants of the new cultivar 'EC-PEPE-2102' are similar to plants of *Peperomia* 'Napoli Nights', U.S. Plant Pat. No. 29,416. However, plants of the new cultivar differ in the following characteristics:

1. Leaves of the new variety are oval-shaped, while leaves of this comparator are oblong with a more pointed tip.
2. Leaves of the new variety have two contrasting colors of dark-green around main leaf veins, and silver-grey in between main leaf veins. Leaf upper side of this comparator is evenly grey-colored.
3. Leaf stems of the new variety are shorter than leaf stems of this comparator.

BRIEF DESCRIPTION OF THE PHOTOGRAPHS

The accompanying photograph in FIG. 1 illustrates in full color a typical plant of 'EC-PEPE-2102' grown in a greenhouse. The plant is approximately 30 weeks of age.

Figure 1:
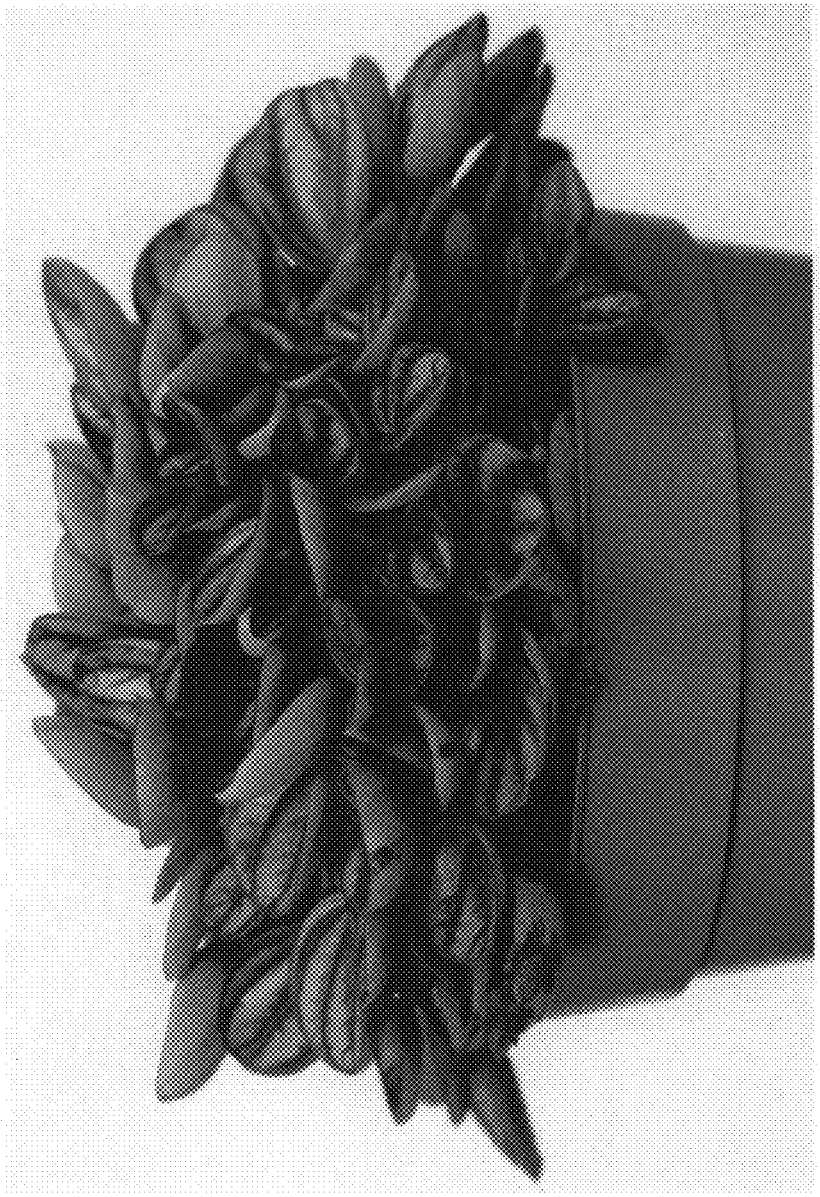
Figure 2:
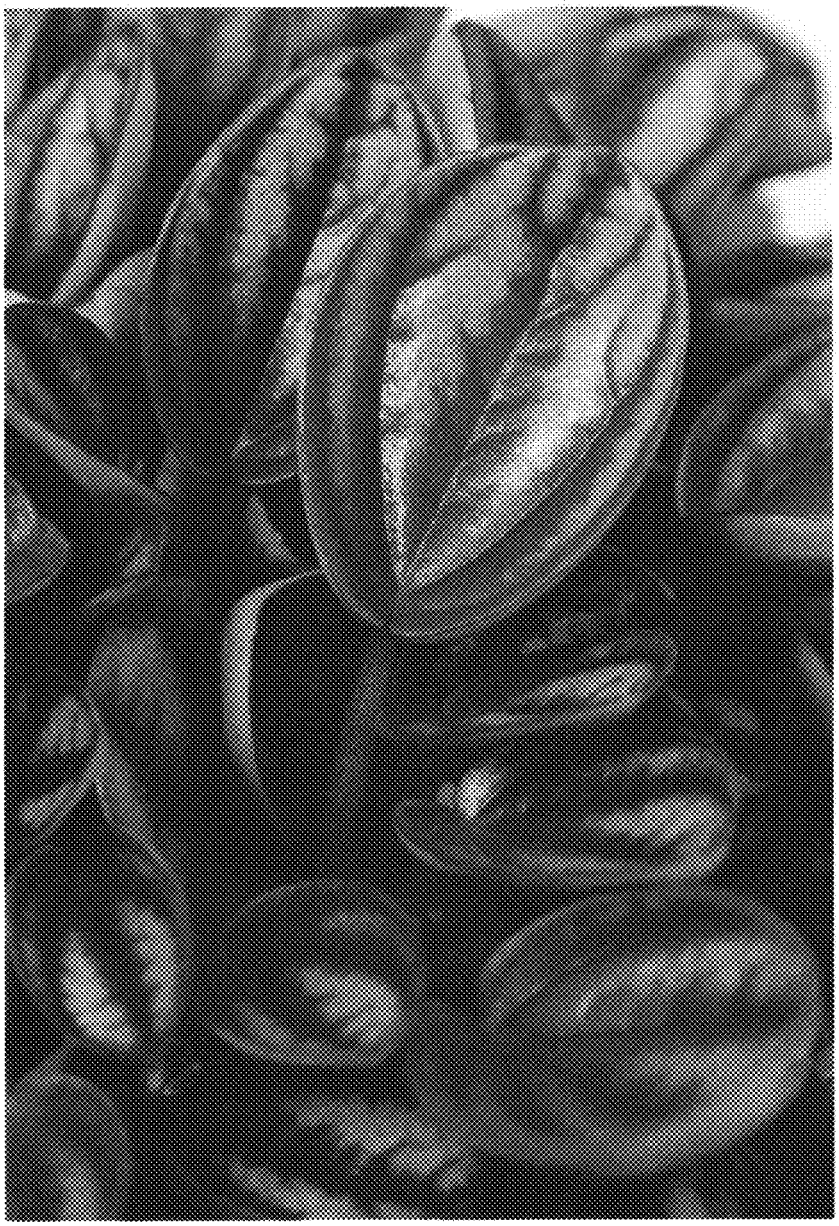
FIG. 2 illustrates a close up of the foliage.
Figure 3:
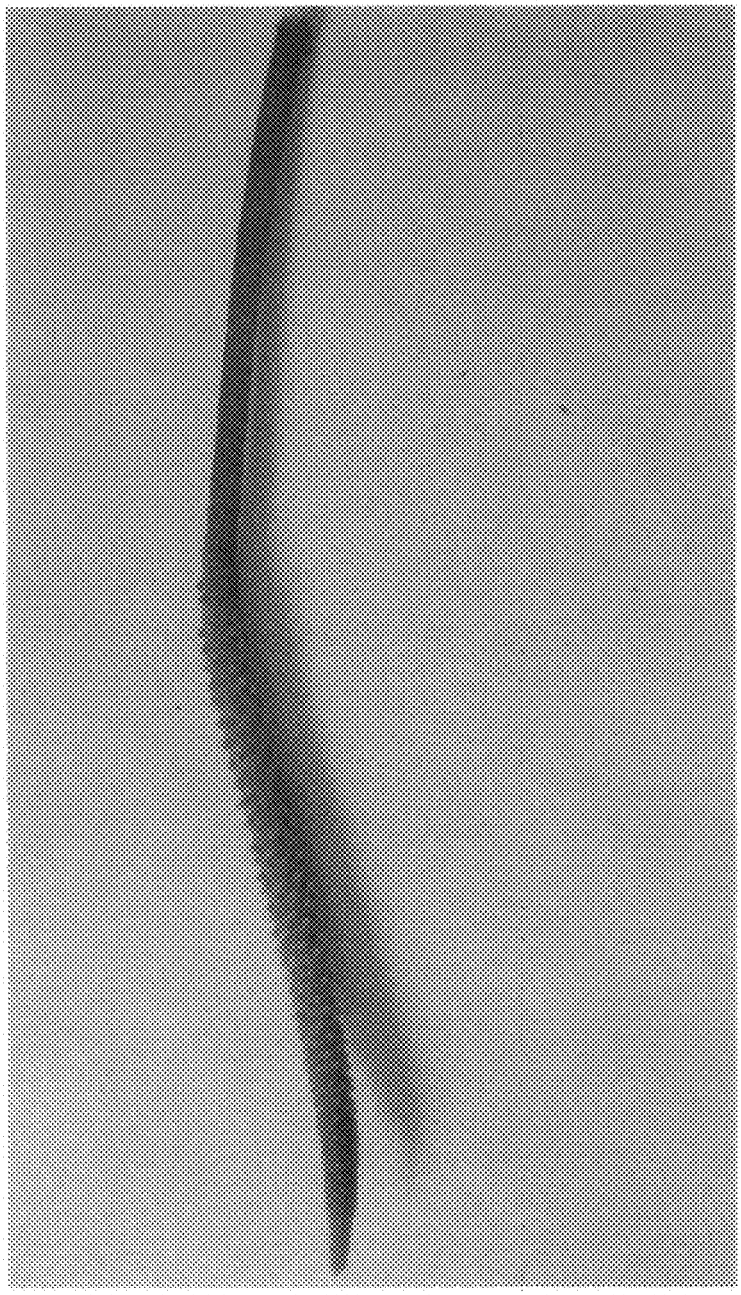
FIG. 3 illustrates a close up of inflorescences.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'EC-PEPE-2102' plants at 10 weeks of age, grown in a greenhouse in Sappemeer, the Netherlands during December. The growing temperature ranged from 17° C. to 20° C. at night to 19° C. to 21° C. during the day. Measurements and numerical values represent averages of typical flowering types.

Botanical classification: *Peperomia caperata* 'EC-PEPE-2102'.

PROPAGATION

Time to initiate roots: About 21 days at approximately 20° C. in summer.

Time to produce rooted cutting: About 25 days at 20° C. in summer.

Description of Roots: Fibrous, fine, moderately dense, freely branching. White in color, not accurately measured with R.H.S. chart.

PLANT

Plant type: Perennial potted plant.

Plant shape: Flattened globular to flattened.

Growth habit: Rosettes of leaves, forming very short, thick stems.

Plant spread: Approximately 22 cm.

Height: 11.2 cm to top of foliar plane.

Growth rate: Moderate.

Plant vigor: Moderate to moderately high.

Age of plant described: Approximately 10 months.

Branching habit: Leaves in rosettes, eventually forming very short, thick stems, branching into lateral rosettes of leaves.

Pinching: Pinching not required.

Number of primary (main) branches per plant: Average 14.

Number of secondary (lateral) branches per plant: Average 12.

Main branches:

*Length*.—Average: 2.4 cm.

*Diameter*.—Average: 0.5 cm.

Internode length: Average: Less than 0.1 cm.

Appearance and shape: Succulent, thick and rounded.

Luster: Matte.

Aspect/angle from vertical: Average angle: 20°.

Strength: Moderately strong.

Color:

*Developing*.—RHS Greyed-Red 178A.

*Mature*.—RHS Greyed-Orange 177A.

*At internodes*.—RHS Greyed-Orange 177A.

Pubescence: None.

Plant fragrance: None.

FOLIAGE

Leaf:

*Arrangement*.—Alternate, single.

*Quantity*.—Average 23.

*Average length*.—3.3 cm.

*Average width*.—2.4 cm.

*Shape of blade*.—Elliptic to near obovate.

*Apex*.—Obtuse.

*Base*.—Deeply truncate to near cordate.

*Margin*.—Entire.

*Texture of top surface*.—Glabrous, smooth, moderately leathery, slightly to moderately bullate.

*Texture of bottom surface*.—Glabrous, smooth, moderately leathery.

*Pubescence*.—None.

*Luster, upper side*.—Moderately glossy.

*Luster, under side*.—Slightly glossy, velvety.

*Color*.—Young foliage upper side: RHS Black 202C, area surrounding veins Greyed-Green N189A. Young foliage under side: RHS Greyed-Green 193A, veined Yellow-Green 148A. Mature foliage upper side: A color between RHS Greyed-Green N189C and Black 202C; area surrounding veins Greyed-Green N189A, and slightly darker. Mature foliage under side: A color between RHS Yellow-Green N148A and Greyed-Green 194A.

*Venation*.—Pattern: Parallel, moderately furrowed. Venation color upper side: RHS Greyed-Green N189A, and slightly darker. Venation color under side: RHS Yellow-Green 148A.

*Petiole*.—Average Length: 6 cm. Diameter: 0.3 cm. Texture: Glabrous, smooth. Luster: Both sides very slightly glossy. Strength: Low. Color, upper side: RHS Yellow-Green 148C, heavily finely-striped Greyed-Red 182A. Color, under side: RHS Yellow-Green 148C, heavily finely-striped Greyed-Red 182A.

FLOWER

Inflorescence:

*Arrangement*.—Axillary spike.

*Inflorescence type and form*.—Spike.

*Inflorescence height*.—Average: 3.9 cm (excl. peduncle).

*Inflorescence diameter*.—Average: 0.25 cm.

*Quantity of flowers per inflorescence*.—Average approximately 425 individual flowers per spike.

Flower bud:

*Flower bud length*.—About 0.75 mm.

*Flower bud diameter*.—About 0.3 mm.

*Flower bud shape*.—Flattened elliptic.

*Flower bud texture*.—Glabrous.

*Flower bud luster*.—Slightly glossy.

*Flower bud color*.—Near Yellow-Green 148C, slightly tinged Greyed-Purple 185A.

Flower:

*Flower type and form*.—Individual flowers are very small and consist of 1 bract and a single pistil. No petals or sepals present.

*Fragrance*.—No fragrance.

*Flower height* (*vertical*).—Average: 0.8 mm.

*Flower diameter* (*horizontal*).—Average: 0.6 mm.

*Flower longevity on plant*.—Average one month.

*Persistent of self-cleaning*?.—Self-cleaning.

Petals: No petals present.

Calyx: No sepals present; no calyx present.

Peduncles:

*Terminal peduncle length*.—Average: 5.8 cm.

*Terminal peduncle diameter*.—Average: 2.0 mm.

*Peduncle angle to lateral branch axis*.—Average angle: 30°.

*Peduncle strength*.—Moderately weak.

*Peduncle texture*.—Glabrous, smooth.

*Peduncle luster*.—Moderately glossy.

*Peduncle color*.—Yellow-Green 147D, slightly finely striped Greyed-Red 182A.

Pedicels: No pedicels present, individual flowers sessile.

Floral bracts: Below each individual flower a single bract is present, shaped orbicular, average length and width: 0.4 mm, colored near Yellow-Green 146D, slightly tinged Greyed-Purple 185A.

Reproductive organs:

*Androecium*.—Not present.

*Gynoecium*.—

*Pistil number* (*per flower*).—1.

*Pistil length*.—Average: 0.1 mm.

*Stigma shape*.—Disc.

*Stigma length*.—Average: 0.1 mm.

*Stigma diameter*.—Average: 0.1 mm.

*Stigma color*.—Near RHS Yellow-Green 146D.

*Style length*.—No style visible, stigma sessile.

*Ovary color*.—Near RHS Yellow-Green 146D.

OTHER CHARACTERISTICS

Seeds and fruits: None observed to date.

Disease/pest resistance: No increased nor decreased resistance nor susceptibility to normal diseases and pests of *Peperomia* has been observed.

Temperature tolerance: Tolerates temperatures up to 40° C. Hardy to USDA zones 10 to 12.

What is claimed is:

1. A new and distinct cultivar of *Peperomia* plant named 'EC-PEPE-2102' as herein illustrated and described.

* * * * *